(12) United States Patent
Challener et al.

(10) Patent No.: US 9,791,619 B2
(45) Date of Patent: Oct. 17, 2017

(54) MICROSTRUCTURED OPTICAL FIBERS FOR GAS SENSING SYSTEMS

(71) Applicant: General Electric Company, Schenectady, NY (US)

(72) Inventors: William Albert Challener, Glenville, NY (US); Niloy Choudhury, Glenville, NY (US); Sabarni Palit, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 59 days.

(21) Appl. No.: 14/876,411

(22) Filed: Oct. 6, 2015

(65) Prior Publication Data

US 2017/0097464 A1    Apr. 6, 2017

(51) Int. Cl.
*G02B 6/032* (2006.01)
*G01N 21/3504* (2014.01)
(Continued)

(52) U.S. Cl.
CPC ........ *G02B 6/02328* (2013.01); *G01J 3/0218* (2013.01); *G01J 3/0221* (2013.01);
(Continued)

(58) Field of Classification Search
CPC ............ G02B 6/02309; G02B 6/02328; G02B 6/02347; C03B 2203/14; C03B 2203/16; C03B 2203/42
See application file for complete search history.

(56) References Cited

U.S. PATENT DOCUMENTS

| 7,343,074 B1 * | 3/2008 | Gallagher | .......... | G01N 21/3504 |
| | | | | 250/227.11 |
| 7,428,360 B2 * | 9/2008 | Gallagher | .......... | G01N 21/3504 |
| | | | | 385/12 |

(Continued)

FOREIGN PATENT DOCUMENTS

| CN | 102193139 | 9/2011 |
| CN | 102279154 | 12/2011 |

(Continued)

OTHER PUBLICATIONS

Hoo et al.; Fast Response Microstructured Optical Fiber Methane Sensor with Multiple Side-Openings; Photonics Technology Letters, IEEE; Mar. 1, 2010; vol. 22, Issue 5, pp. 296-298.

(Continued)

*Primary Examiner* — Michelle R Connelly
(74) *Attorney, Agent, or Firm* — Pabitra K. Chakrabarti

(57) ABSTRACT

Microstructured optical fiber (MOF) includes a cladding extending a length between first and second ends. The cladding includes an inner porous microstructure that at least partially surrounds a hollow core. A perimeter contour of the hollow core has a non-uniform radial distance from a center axis of the cladding such that first segments of the cladding along the perimeter contour have a shorter radial distance from the center axis relative to second segments of the cladding along the perimeter contour. The cladding receives and propagates light energy through the hollow core, and the inner porous microstructure substantially confines the light energy within the hollow core. The cladding defines at least one port hole that extends radially from an exterior surface of the cladding to the hollow core. Each port hole penetrates the perimeter contour of the hollow core through one of the second segments of the cladding.

7 Claims, 11 Drawing Sheets

(51) Int. Cl.
  *G02B 6/02* (2006.01)
  *G01J 3/02* (2006.01)
  *G01N 21/03* (2006.01)

(52) U.S. Cl.
  CPC ..... *G01N 21/0303* (2013.01); *G01N 21/3504* (2013.01); *G02B 6/02309* (2013.01); *G02B 6/02347* (2013.01); *G02B 6/02371* (2013.01); *G01N 2201/08* (2013.01); *G01N 2201/088* (2013.01)

(56) References Cited

U.S. PATENT DOCUMENTS

| | | | |
|---|---|---|---|
| 8,133,593 B2* | 3/2012 | Carberry | G01N 21/05 385/123 |
| 9,031,372 B2 | 5/2015 | Mukasa | |
| 2004/0096173 A1* | 5/2004 | Fekety | B82Y 20/00 385/125 |
| 2006/0104582 A1 | 5/2006 | Frampton et al. | |
| 2008/0205837 A1* | 8/2008 | Gallagher | G01N 21/3504 385/124 |
| 2012/0141081 A1* | 6/2012 | Dangui | G02B 6/02042 385/126 |
| 2015/0198764 A1* | 7/2015 | Digiovanni | C03B 37/01217 385/125 |

FOREIGN PATENT DOCUMENTS

| | | |
|---|---|---|
| CN | 102359955 | 2/2012 |
| CN | 103323422 | 9/2013 |
| WO | 04001465 | 12/2003 |
| WO | 2009029987 | 3/2009 |

OTHER PUBLICATIONS

Jin et al.; Gas detection with micro- and nano-engineered optical fibers; Optical Fiber Technology; Dec. 2013; vol. 19, Issue 6, Part B, pp. 741, 759.

Debord et al. Hypocycloid-shaped hollow-core photonic crystal fiber Part I: Arc curvature effect on confinement loss; Optics Express; Nov. 18, 2015; vol. 21, No. 23; 12 pages.

Hensley et al.; Photonic band-gap fiber gas cell fabricated using femtosecond micromachining; Optics Express; May 28, 2007; vol. 15, No. 11, pp. 6690-6695.

Brakel et al.; Micro-channels machined in microstructed optical fibers by femtosecond laser; Optics Express; Jul. 9, 2007; vol. 15, No. 14, pp. 8731-8736.

* cited by examiner

MICROSTRUCTURED OPTICAL FIBERS FOR GAS SENSING SYSTEMS

GOVERNMENT LICENSE RIGHTS

This invention was made with government support under DE-AR0000543 awarded by the Department of Energy. The government has certain rights in the invention.

BACKGROUND

Various devices have been developed for sensing and measuring the concentrations of different gases at man-made or natural locations, such as oil wells, pipelines, mines, manufacturing plants, refineries, and the like. Monitoring for the presence and concentration of gases may be used for various applications, such as to ensure that toxic gases (CO, $H_2S$, etc.) are not present in significant concentrations, to ensure that explosive gases ($CH_4$, $H_2$, etc.) are below respective explosive limits, to identify the gases in a mixture (for custody transfer, heat content, etc.), or for various other reasons. Spectroscopy may be used to provide highly sensitive and selective sensors because each gas exhibits a unique spectroscopic fingerprint, such that gases absorb and emit light energy at specific wavelengths. Gases are relatively transparent, however, so the absorption line strength of a gas may be relatively small and hard to detect.

To accommodate for the small absorption line strength, light used in spectroscopy is required to pass through long path lengths in the gas in order to establish sufficient sensitivity for spectroscopic sensor to provide a measurement of a concentration of a gas of interest in a test sample, for example. For example, a light source of the spectroscopic sensor may be separated from a detector of the spectroscopic sensor by a distance of one kilometer or more to achieve a necessary path length, but such distances are not practical in most applications.

Other known types of spectroscopic sensors define an optical cavity with two mirrors and are referred to as optical cavity sensors. The gas is contained within the optical cavity, and the light is reflected between the two mirrors multiple times before being detected. While this technique allows for a manageable device size, it is problematic due to the need to maintain very exacting alignment of the mirrors. Variations in conditions, such as temperature changes, vibration, humidity, or the like, may misalign the mirrors or otherwise interfere with the sensitivity and/or accuracy of these optical cavity sensors. Therefore, this technique is generally not used for remote, unattended measurements in various field environments, such as an oil or gas well pad, a pipeline, a mine, or the like. Moreover, optical cavity sensors are generally quite expensive.

BRIEF DESCRIPTION

A microstructured optical fiber (MOF) is provided that includes a cladding with an outer solid silica layer and, an inner porous microstructure, and a hollow core. The porous microstructure of the cladding surrounds a hollow core. The hollow core is configured to receive and propagate light energy along at least a portion of a length of the fiber. The inner porous microstructure of the cladding confines the light energy within the hollow core. Port holes are periodically inserted radially through the cladding into the hollow core. The port holes enable gas to diffuse into the hollow core from an external environment outside of the fiber to interact with the light energy within the hollow core.

In one embodiment, the perimeter between the core and porous microstructure of the cladding is composed of segments of silica with negative curvature such that a finite number of points or segments along the perimeter are located at a minimum radius from the center of the core, while all other portions of the perimeter are at greater distances from the center of the core. The port holes are inserted through the cladding at locations which intersect the perimeter of the core at or near the points on the perimeter that are at a maximum distance from the center of the core.

In another embodiment, a microstructured optical fiber (MOF) is provided with a porous cladding microstructure that supports an antisymmetric propagating electromagnetic mode, a mode in which the field goes to zero at some points within the core and on its perimeter. The perimeter of the hollow core may have, for example, an oblong shape including a narrow section between two wide sections. The port holes are inserted through the cladding into the core at or near the points on the perimeter that are at a null of the electromagnetic field.

In one embodiment, a microstructured optical fiber (MOF) is provided that includes a cladding extending a length between a first end and an opposite second end. The cladding includes an inner porous microstructure that at least partially surrounds a hollow core through the cladding. The cladding defines a perimeter contour of the hollow core. The perimeter contour of the hollow core has a non-uniform radial distance from a center axis of the cladding such that first segments of the cladding along the perimeter contour have a shorter radial distance from the center axis relative to second segments of the cladding along the perimeter contour. The cladding is configured to receive and propagate light energy through the hollow core. The inner porous microstructure is configured to substantially confine the light energy within the hollow core. The cladding defines at least one port hole that extends radially from an exterior surface of the cladding to the hollow core. Each port hole penetrates the perimeter contour of the hollow core through one of the second segments of the cladding.

In another embodiment, a microstructured optical fiber (MOF) is provided that includes a cladding extending a length between a first end and an opposite second end. The cladding defines an inner porous microstructure that at least partially surrounds a hollow core through the cladding. The cladding defines a perimeter contour of the hollow core. The perimeter contour of the hollow core has an oblong shape including a narrow section between two wide sections. The cladding is configured to receive and propagate light energy through the hollow core. The inner porous microstructure is configured to substantially confine the light energy within the hollow core. The cladding further defines at least one port hole that extends radially from an exterior surface of the cladding through the inner porous microstructure to the hollow core. Each port hole penetrates the perimeter contour of the hollow core at the narrow section. The at least one port hole is sized to allow gas into the hollow core from an external environment outside of the exterior surface of the cladding.

In another embodiment, a gas sensing system is provided that includes a microstructured optical fiber (MOF) and a light source. The MOF extends between a first end and an opposite second end. The MOF includes an outer solid cladding and an inner porous microstructure cladding circumferentially surrounded by the outer solid cladding. The inner porous microstructure cladding surrounds a hollow core. The inner porous microstructure cladding includes thin walls that define a perimeter contour of the hollow core. The MOF defines port holes spaced apart from each other along the length of the MOF. The port holes extend radially through the outer solid cladding and the inner porous microstructure cladding from an exterior surface of the outer solid cladding to the hollow core. The light source is optically coupled to the first end of the MOF and configured to provide light energy into the hollow core. The hollow core is configured to receive and propagate the light energy towards the second end of the MOF. The inner porous microstructure cladding is configured to substantially confine the light energy within the hollow core. The perimeter contour of the hollow core defines a high electric field area and a low electric field area such that a majority of the light energy propagating through the hollow core extends through the high electric field area and a minority of the light energy extends through the low electric field area. The port holes of the MOF penetrate the perimeter contour of the hollow core at the low electric field area. The port holes are configured to allow gas into the hollow core from an external environment outside of the exterior surface of the outer solid cladding to interact with the light energy within the hollow core.

DETAILED DESCRIPTION

Figure 1:
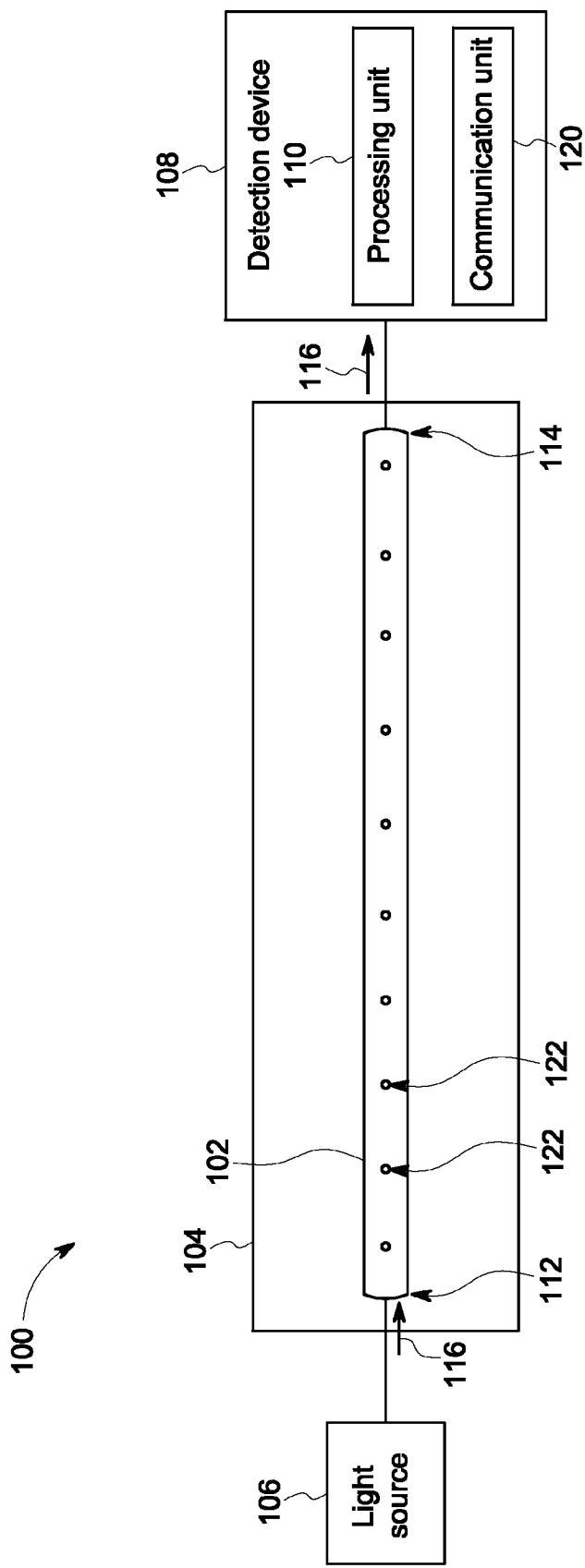
FIG. 1 is a schematic view of a gas sensing system formed in accordance with one or more embodiments.

Various embodiments will be better understood when read in conjunction with the appended drawings. To the extent that the figures illustrate diagrams of the functional blocks of various embodiments, the functional blocks are not necessarily indicative of the division between hardware (including circuitry). Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "device" may include a hardware and/or software system that operates to perform one or more functions. For example, a device, unit, or system may include one or more computer processors, microprocessors, field programmable gate arrays, integrated circuits, controllers, or other logic-based devices that perform operations based on instructions stored on a tangible and non-transitory computer readable storage medium, such as a computer memory. Alternatively, a device, unit, or system may include a hard-wired device that performs operations based on hard-wired logic of the device. The device or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide for gas sensing systems and methods using hollow core microstructured optical fibers. The hollow core microstructured optical fibers can be used to replace the optical cavity in a spectroscopic sensor while maintaining the long optical path length and, hence, sensitivity of the sensing system, without requiring a great distance for the optical path length. The optical fibers may not require sensitive alignment, and can be suitable for long term, remote, unattended sensor operation. The gas sensing systems disclosed herein may be manufactured for less cost than some known spectroscopic sensors.

The gas sensing systems and methods described herein may be used to detect and measure concentrations of gases of interest in various applications. For example, the gas sensing system may be used to monitor gases at oil wells or well pads, along pipelines, in mines, in manufacturing plants, at refineries, in factories, and the like. One particular application is measurement of fugitive methane emissions from oil and gas well pads. Methane is a strong contributor to the greenhouse effect, which traps infrared radiation within the earth's ozone layer. The low cost, but highly sensitive (~10 parts per million, or ppm) gas sensing systems described herein may be disposed at oil and gas well pads to monitor methane emissions. The monitoring of methane emissions may be in order to comply with regulations designed to reduce greenhouse gas emissions, to reduce loss of methane that could be sold as product, or the like. Although the gas sensing system is located in the field at the oil and gas well pad, the gas sensing system may be monitored remotely, allowing for remote monitoring of multiple gas sensing systems at different oil and gas well pads, for example.

Spectroscopy can be used for gas sensing by detecting the wavelengths that gas samples absorb and emit light energy. These wavelengths, referred to as absorption spectra, are specific or unique to the types of gases. For example, methane has several absorption bands at different wavelengths, such as a weak absorption band at 1.6 microns in the near infrared (NIR) range, and a stronger absorption band between 3.2 and 3.3 microns in the mid-IR range. As referred to herein, the mid-IR range is generally considered to be between 2 and 10 microns. In addition to methane, various other gases have relatively strong absorption bands in the mid-IR range, such as ammonia, carbon dioxide, water vapor, and carbon monoxide. Therefore, the gas sensing systems described herein are designed to operate within the mid-IR range, where absorption bands of several potential gases of interest are strong. Since gases are relatively transparent, sensing systems detect gases with better accuracy and sensitivity at wavelengths where the gases have strong absorption bands compared to wavelengths where the gases have weak absorption bands.

Solid core optical fibers, such as fibers with silica cores, are less transparent in the mid-IR range than the NIR range. As a result of higher absorption loss, the solid core optical fibers are not able to transmit light in the mid-IR range.

Figure 2:
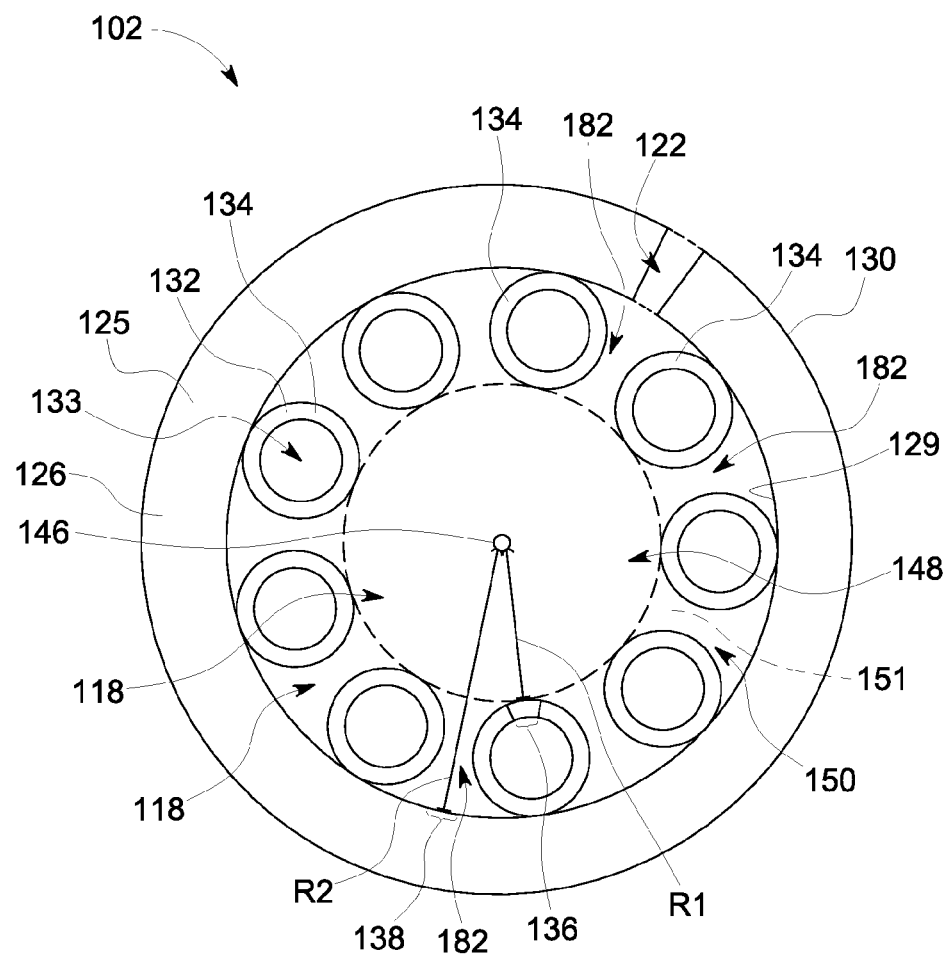
FIG. 2 is a cross-sectional view of a microstructured optical fiber (MOF) of the gas sensing system shown in FIG. 1 according to one embodiment.
Figure 3:
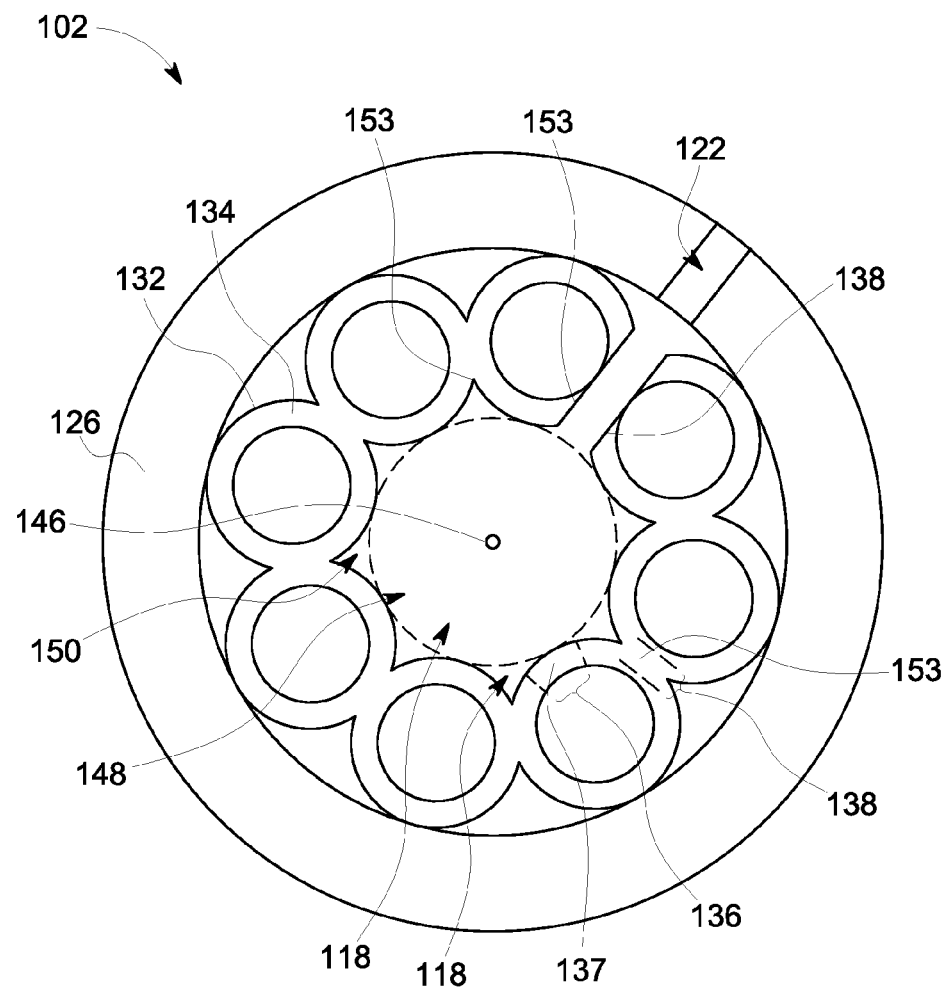
FIG. 3 is a cross-sectional view of the MOF of the gas sensing system of FIG. 1 according to an alternative embodiment.

Microstructured (or "holey") optical fibers, on the other hand, have fiber structures that are porous and make use of this porosity in several different ways to confine light to the core of the fiber so that it can propagate for long distances along the fiber. Hollow core microstructured fibers are designed in several different ways to confine at least most of the electric field of the light wave inside hollow gas-filled cores instead of solid silica, which obviates or at least reduces the problem of absorption loss in silica. In one type of hollow core microstructured fiber, for example, the thin glass wall of the microstructure surrounding the center hollow core is composed of multiple connected segments with "negative curvature." Examples of this type of hollow core microstructured fiber are shown in FIGS. 2 and 3. The microstructure with negative curvature is generally designed to substantially confine light in the core as it propagates along the fiber through an antiresonance effect. In another type of hollow core microstructured fiber shown in FIG. 4, the hollow core is surrounded by a regular lattice of smaller holes that act to generate a "photonic bandgap" in order to substantially confine light in the core as it propagates along the fiber. One advantage of hollow core microstructured fibers is that the region of strong electric fields from the light wave propagating inside the hollow core overlaps and interacts with relatively small regions of the thin silica wall nearest to the center core. This reduced interaction between the strong electric fields and the thin silica walls that define the center core reduces the absorption losses of the fiber from interaction of the light wave with the silica and enables much longer distances of light propagation within the fiber. For example, the microstructured optical fibers may be configured to convey light in the mid-IR range for up to 100 meters (m) or more. Depending on the absorption band strength of a particular gas of interest, the path length of the microstructured optical fiber in one or more of the gas sensing systems disclosed herein may be shorter than 100 m, such as 10 m or less. The short lengths of fiber required, as well as the fact that the fibers optionally may be coiled, allows the gas sensing systems to be packaged in relatively compact cases for portability. For example, the case for a gas sensing system may be a cubic foot or less, and easily carried by hand.

In order to perform spectroscopy measurements on gases in the hollow core of a microstructured optical fiber, the fiber has to permit gas into the hollow core. Typical microstructured optical fibers are only open at the ends, so gas sensing can be performed by allowing gas to diffuse into the hollow core from the ends of the fiber. It is more beneficial to be able to detect gas along the length of the fiber to increase the monitoring area and reduce the number of discrete gas sensing systems required. For example, in order to monitor for gas leaks along a pipeline or an oil or gas well pad, where potential leak spots are unknown, detection of gas along the length of the fiber is desirable. Thus, in gas sensing systems disclosed herein, gas is permitted into the hollow core along the length of the microstructured optical fiber through port holes.

Holes may be drilled from the outer perimeter of the fiber into the core at various spaced apart locations along the length of the fiber to allow gas to diffuse from the external environment into the hollow core. See, for example, Hensley et al., "Photonic band-gap fiber gas cell fabricated using femtosecond micromachining," *Opt. Exp.* 15 (2007) 6690, or Brakel et al., "Micro-channels machined in microstructured optical fibers by femtosecond laser," *Opt. Exp.* 15 (2007) 8731. However, the drilled holes penetrate the silica microstructure surrounding the hollow core, which may disturb the ability of the microstructure to confine light within the core. The holes may become scattering sites that emit light from the fiber and greatly reduce the distance over which the light wave can propagate through the fiber. With increasing numbers of holes, the amount of light emitted from the core increases such that there is not enough light left in the hollow core at the end of the fiber for a spectroscopy measurement.

In various embodiments described herein, microstructured optical fibers include port holes (for allowing gas into the hollow core) that are specifically located and oriented relative to the microstructure to reduce the effect of the port holes on the light propagating through the core. The port holes are designed to reduce light scattering that causes electromagnetic energy loss. By reducing the light energy lost attributable to the port holes, the microstructured optical fibers may include more port holes along the length of the fibers which increases the overall rate at which gas will diffuse into the core.

At least one technical effect of various embodiments described herein includes providing gas sensing along a length of a microstructured optical fiber, where the fiber conveys light in the mid-IR range for highly sensitive and selective detection of various gases of interest. At least one technical effect of various embodiments includes microstructured optical fibers that have port holes spaced apart along the length of the fibers to allow gas into the hollow core of the fibers with a negligible or at least smaller effect on reduction of light propagation within the core. For example, the microstructured optical fibers disclosed herein may enable low loss port hole penetrations for gas sensing applications. In another example, the microstructured optical fibers may enable a waveguide mode that minimizes (or at least reduces) interaction of the electric field of the electromagnetic wave with port holes for gas diffusion into the fiber core. Another technical effect of various embodiments includes detecting gases of interest along an extended length instead of at one or two particular points. Still another technical effect of various embodiments is providing gas sensing systems that are relatively compact, low cost, and able to withstand harsh environmental conditions (e.g., large temperature changes, moisture, contaminants, etc.).

FIG. 1 is a schematic view of a gas sensing system 100 formed in accordance with one or more embodiments. The gas sensing system 100 is configured to detect the presence and/or concentration of one or more gases of interest along a remote test location 104. The depicted gas sensing system 100 is configured to monitor for the gases of interest along a length of a cable disposed in the test location 104. The test location 104 may be subject to environmental conditions that may be damaging to certain electronic equipment, such as thermocouples. For example, the test location 104 may be a geothermal well, oil and/or gas well, oil and/or gas well pad, oil and/or gas pipeline, a mine, or the like. The test location 104 in other examples may be an industrial facility, such as a manufacturing plant, a refinery, or a factory. As one more example, the test location 104 may be a wellbore used in conjunction with hydraulic fracturing. The test location 104 depicted in FIG. 1 is shown as having a generally horizontal configuration for clarity and ease of illustration. However, in various embodiments, the test location 104 may also have vertically oriented portions or volumes.

The test location 104 may be understood as being remote in that the test location 104 is located at a distance from components of the gas sensing system 100 configured to generate and/or receive signals conveyed through the test location 104. Thus, signal generation and/or signal processing equipment, for example, may be maintained under different environmental conditions than the components of the gas sensing system 100 along the remote test location 104. Alternatively, signal generation and/or signal processing components of the gas sensing system 100 may be located at the remote test location 104, and may be housed within protective cases or housings to protect such components from the environmental conditions of the test location 104, such as hot and cold temperatures, moisture, debris, vibration, and the like.

The gas sensing system 100 depicted in FIG. 1 includes a microstructured optical fiber 102, a light source 106, a detection device 108, and a processing unit 110. The microstructured optical fiber 102 is referred to herein as "MOF 102". Although not shown, the MOF 102 optionally may be part of a cable such that the MOF 102 is enclosed within a protective sheath that is permeable or porous to gas diffusion. Although one MOF 102 is shown and described, a cable may include multiple MOFs 102 in a fiber bundle that extends along the test location 104. The MOF 102 extends a length between a first end 112 and an opposite second end 114. The length may be up to 100 m or more. For example, the MOF 102 may be about 1 m long, about 10 m long, or about 80 m long. The MOF 102 is not shown to scale in FIG. 1.

The light source 106 and the detection device 108 are optically coupled to the MOF 102. For example, the light source 106 is optically coupled to the first end 112 of the MOF 102, and the detection device 108 is optically coupled to the second end 114. As used herein, two components are "optically coupled" when at least a majority of light being emitted from one of the components is received at the other component. In addition to being optically coupled, the light source 106 and/or the detection device 108 may be mechanically coupled, directly or indirectly, to the MOF 102. Generally, in various embodiments, the light source 106 is configured to generate light 116 (also referred to as "light energy") that is transmitted to the MOF 102. The light source 106 may be a laser that emits light in the infrared range, such as the mid-IR range. The light 116, for example, may have a predetermined pulse length or wavelength. In an embodiment, the light has a wavelength in the infrared range. More specifically, the light has a wavelength in the mid-IR range, such as between 2 and 10 microns. Thus, the light or light energy 116 may not be visible light.

The MOF 102 includes a hollow core 118 (shown for example in FIG. 2) that extends along the entire length of the MOF 102. The core 118 receives the light 116 at the first end 112. The core 118 may have a diameter between 10 and 200 micrometers, such as around 50 micrometers. In an embodiment, the MOF 102 also includes a plurality of port holes 122 that extend from an exterior surface of the MOF 102 into the core 118. The port holes 122 are spaced apart along the length of the MOF 102. For example, the port holes 122 may be spaced apart by 0.5 m, 1 m, or 2 m. The port holes 122 are sized to allow for gas in the external environment to diffuse through the port holes 122 into the core 118, where the gas can interact with the light 116 propagating through the core 118. As used herein, "interaction" of a gas with the light 116 involves the absorption and emission of light energy by the gas at various wavelengths, which affects and/or alters the characteristics of the light energy propagating through the hollow core 118. The port holes 122 may have a diameter between 1 and 50 micrometers, for example, such as 10 micrometers. The port holes 122 may be small enough to restrict liquids and solids from entering the core 118 through the holes 122. Although the port holes 122 are shown as generally circular in the illustrated embodiment, the port holes 122 optionally may have an oblong shape such that the port holes 122 are longer along the length of the fiber 102 than in a perpendicular direction along the circumference of the fiber 102. The port holes 122 may also be conical such that the diameter of the port hole 122 where it intersects the core 118 is smaller than the diameter of the port hole 122 where it intersects an outer surface of the fiber 102.

The light 116 propagates through the core 118 to the second end 114, where the light 116 is detected by the detection device 108 as optical signals. The optical signals are responsive to and representative of the light 116 interacting with one or more gases in the hollow core 118 (shown in FIG. 2). The detection device 108 may be an optical sensor, an optical camera, or the like, configured for use in infrared gas-phase spectroscopy. The processing unit 110 is operably connected to the detection device 108. In an alternative embodiment, instead of being located at the second end 114, the detection device 108 is located at the first end 112 with the light source 106. A mirror (not shown) may be placed at the second end 114 to reflect light back to the first end 112. In such case, a power splitter or an optical circulator can be used to split the reflected light off to the detection device 108.

The processing unit 110 includes one or more processors. As shown in FIG. 1, the processing unit 110 may be a component of the detection device 108, such that the processing unit 110 is contained within a housing of the detection device 108. In an alternative embodiment, the processing unit 110 is located remote from the detection device 108, and is operably connected via a wired connection or a wireless connection. For example, the detection device 108 may include a communication unit 120 that is configured to transmit (and optionally receive) the received optical signals to one or more processors at a remote location. The communication unit 120 may include a transmitter or a transceiver and associated circuitry.

The processing unit 110 is configured to determine a presence and/or a concentration of one or more gases in the MOF 102 based on the optical signals received by the detection device 108. For example, the processing unit 110 may be configured to analyze the optical signals to identify various gases of interest within the MOF 102 that interacted with the light 116 to detect the presence of such gases. The processing unit 110 may analyze the optical signals using algorithms known in the art for gas-phase IR spectroscopy. For example, the processing unit 110 may compare the detected wavelengths of absorption bands in the test sample to known absorption band wavelengths of known gases in order to identify one or more gases in the test sample. In addition to identifying the gases, the processing unit 110 may also determine the concentrations of the gases. The processing unit 110 may determine that the gas in the MOF 102 includes water vapor, carbon dioxide, methane, and ethane, for example, and may also detect the concentrations and/or relative concentrations of these identified gases. For example, the processing unit 110 may determine that a first sample of gas includes 2 parts per million of methane, which is a typical level in the atmosphere. The processing unit 110 may subsequently measure a second sample of gas to include 200 ppm of methane, indicating a spike in concentration potentially due to a leak. The processing unit 110 may be configured to generate a control signal in response to detecting the spike in methane concentration, such as to send an alert. The processing unit 110 may also generate other control signals responsive to detecting one or more gases of interest, such as for automatically scheduling additional inspection, to initiate a shutdown of the well, to activate a system that stops methane leaking or egress, or the like.

FIG. 2 is a cross-sectional view of the MOF 102 of the gas sensing system 100 shown in FIG. 1 according to one embodiment. The MOF 102 includes a cladding 125 that extends a length of the fiber 102, such as between the first and second ends 112, 114 shown in FIG. 1. The cladding 125 defines the shape and perimeter of the hollow core 118, referred to as the perimeter contour of the hollow core 118. The cladding 125 is configured to receive and propagate light energy through the hollow core. The cladding 125 includes an inner porous microstructure layer 132, which is also referred to herein as an inner microstructure 132 and an inner porous microstructure 132. At least most of the perimeter contour of the hollow core 118 is defined by the inner porous microstructure 132. The inner porous microstructure 132 is configured to substantially confine the light energy propagating through the fiber inside the core 118 of the MOF 102.

The inner porous microstructure 132 includes holes 133 extending the length of the inner portion microstructure 132 that may be arranged in a regular lattice or may be arranged in other ways. The holes 133 may be circular or non-circular. In one embodiment, at least some of the holes 133 are defined within hollow rings 134 that are arranged in an annular array. The rings 134 may be formed of silica or a similar material. The hollow rings 134 do not transmit significant light energy through the holes 133 within the rings 134 because the holes 133 are substantially smaller than the size of the hollow core 118. For example, the hollow core 118 may have a diameter of around 50 micrometers, while the holes 133 may have a size on the order of 0.5 to 5 micrometers. In the illustrated embodiment, the rings 134 are separated from adjacent rings 134 by gaps 182.

As shown in FIG. 2, the cladding 125 optionally also includes an outer solid layer 126 that circumferentially surrounds the inner porous microstructure layer 132. The outer solid layer 126 may be composed of solid silica or a similar material. The inner porous microstructure 132 is an interior layer of the cladding 125, and the outer solid layer 126 is an outer layer of the cladding 125. The outer solid layer 126 includes an exterior surface 130 and an interior surface 129. The exterior surface 130 of the outer cladding 126 defines the outer perimeter of the MOF 102. The inner porous microstructure 132 extends radially inward from the interior surface 129 of the outer cladding 126. The outer cladding 126 may provide structural strength for the MOF 102 and also may shield the inner porous microstructure 132 from impact forces, contaminants, and the like. Optionally, the outer cladding 126 may be surrounded by a plastic sheath (not shown) to prohibit scratches, protect the fiber 102 from humidity, and the like.

In one or more embodiments described herein, the perimeter contour of the hollow core 118 has a non-uniform radial distance from a center axis 146 of the cladding 125 such that different sections or portions of the perimeter contour are closer to the center 146 than other sections or portions of the perimeter contour. The center axis 146 may also be referred to herein as radial center 146. For example, some locations or points along the perimeter are at greater distances from the center 146 of the core 118 than other locations or points along the perimeter. A finite number of points or segments along the perimeter are located at a minimum radius (or radial distance) from the center 146, and all other points or segments are located at greater radial distances from the center 146. Likewise, a finite number of different points or segments along the perimeter are located at a maximum radial distance from the center 146, while all other points or segments, including the points or segments at the minimum radius, are located more proximate to the center axis 146.

In an embodiment, the perimeter contour of the hollow core 118 is composed of multiple segments with at least some of them exhibiting negative curvature. Unlike a typical circular core, which has a positive curvature along its entire perimeter, the perimeter contour of negative curvature hollow cores has a curvature that moves away from a center axis of the core on either side of its closest approach. Thus, the ends of a negative curvature segment of a silica wall are farther from the center axis of the hollow core 118 than the middle portion of the segment between the ends. Although not shown, a hollow core 118 with a square or rectangular perimeter contour also has negative curvature as defined herein.

In the illustrated embodiment, the hollow core 118 extends into the gaps 182 between adjacent rings 134 of the inner porous microstructure 132. Some areas of the hollow core 118 extend radially from the center axis 146 through the gaps 182 to the interior surface 129 of the outer solid layer 126. Thus, the perimeter contour of the hollow core 118 is partially defined by the rings 134 and also partially defined by segments of the interior surface 129 of the outer solid layer 126 that align with the gaps 182 between the rings 134. The perimeter contour of the hollow core 118 has a negative curvature. As shown in FIG. 2, first segments 136 of the cladding 125 along the perimeter contour have a shorter radial distance R1 from the center axis 146 relative to second segments 138 of the cladding 125 along the perimeter contour, which have a greater radial distance R2 from the center axis 146. The first segments 136 are defined by walls of the rings 134 of the inner porous microstructure 132. For example, the first segments 136 are proximate portions of the rings 134 that are proximate to the center axis 146. The first segments 136 may be at a minimum radial distance from the center axis 146 compared to other points along the perimeter contour of the hollow core 118. The second segments 138 are defined by the interior surface 129 of the outer solid layer 126 between the rings 134. The second segments 138 define points along the perimeter contour of the hollow core 118 that are at a maximum radial distance from the center axis 146.

The cladding 125 defines at least one port hole 122 that extends radially from an exterior surface 130 of the cladding 125 to the hollow core 118. Each port hole 122 penetrates the perimeter contour of the hollow core 118 through one of the second segments 138 of the cladding 125. In the illustrated embodiment, the port hole 122 extends through the outer solid layer 126 from the exterior surface 130 to the interior surface 129. The port hole 122 is aligned with one of the gaps 182 between the rings 134. Thus, the port hole 122 penetrates the perimeter contour of the hollow core 118 at a location that is relatively far from the radial center 146, if not at the maximum radial distance from the radial center 146. The port hole 122 is sized to allow gas into the hollow core 118 from outside of the MOF 102. For example, the port hole 122 may have a diameter between 2 and 50 micrometers.

FIG. 2 also depicts an electric field profile for the primary mode of light energy within the hollow core 118. The electric field of a light wave propagating through the core 118 decreases with radial distance from the center axis 146 of the core 118. For example, the maximum electric field occurs along the center axis 146 and is very small at the interior surface 129 of the outer solid layer 126. Thus, the light wave propagating through the core 118 interacts primarily with the portions of the rings 134 of the inner porous microstructure 132 that face the center axis 146. Only a small portion of the light penetrates the gaps 182 and interacts with the interior surface 129 in the regions between the rings 134. The perimeter contour of the hollow core 118 defines a high electric field area 148 radially interior of the first segments 136 of the perimeter contour. The high electric field area 148 is a circular region radially interior of the rings 134, which is where most of the electric field of the light wave is disposed. As is shown in FIG. 3, most of the area of the hollow core 118 is the high electric field area 148. The perimeter contour of the hollow core 118 also defines a low electric field area 150 that is radially exterior of the high electric field area 148. A circular boundary 151 between the high electrical field area 148 and the low electrical field area 150 is shown in FIG. 2 for illustration purposes. The low electric field area 150 is at least partially defined by the second segments 138 of the perimeter contour. For example, the low electric field area 150 is defined along the gaps 182 from the interior surface 129 of the outer solid layer 126 radially inwards to the first segments 136 of the inner porous microstructure 132 that define the boundary 151 of the high electric field area 148. A majority of the light energy in the hollow core 118 is disposed within (for example, passes through) the high electric field area 148 relative to the low electric field area 150.

The port hole 122 penetrates the perimeter contour of the hollow core 118 by extending through the one of the second segments 138 (for example, the interior surface 129 of the outer solid layer 126 between two rings 134), which is in the low electric field area 150. The port hole 122 does not interfere with the high electric field area 148, so the port hole 122 has a low or negligible effect on the majority of the light energy propagating through the core 118. Thus, forming the port holes 122 to penetrate the interior surface 129 in one of the gaps 182 defined by the inner porous microstructure 132 reduces light scatter and attenuation, allowing for more light energy to reach the detection device 108 (shown in FIG. 1) for better gas sensing performance.

Electromagnetic modeling shows that the port hole 122 extending through the interior surface 129 of the outer solid layer 126 of the cladding 125 between the rings 134 as shown in FIG. 2 has almost negligible effect on the lowest order propagating mode as indicated by a very small change in calculated mode index of the fiber before and after forming the port hole 122.

FIG. 3 is a cross-sectional view of the MOF 102 of the gas sensing system 100 of FIG. 1 according to an alternative embodiment. The MOF 102 shown in FIG. 3 is similar to the MOF 102 shown in FIG. 2, except adjacent rings 134 of the inner porous microstructure 132 engage one another at interfaces 153. Therefore, the hollow core 118 does not extend through any gaps to the outer solid layer 126, so the perimeter contour of the hollow core 118 is defined entirely by the inner porous microstructure 132. The perimeter contour of the hollow core 118, like the MOF 102 shown in FIG. 2, is non-uniform with different locations or points along the perimeter contour having varying radial distances from the center axis 146. For example, the perimeter contour in the illustrated embodiment is defined by portions of the rings 134 that have negative curvatures. First segments 136 of the inner porous microstructure 132 have a shorter radial distance from the center axis 146 than second segments 138 of the inner porous microstructure 132 along the perimeter contour of the hollow core 118. In the illustrated embodiment, the first segments 136 are middle segments 137 of the portions of the rings 134 between the two interfaces 153 that are curved towards the center axis 146. Each of the second segments 138 includes an interface 153 between two rings 134. Thus, the middle segments 137 are closer to the radial center 146 than the interfaces 153. The interfaces 153 are the farthest points from the center axis 146 along the perimeter contour of the hollow core 118.

The high electric field area 148 of the light energy propagating through the MOF 102 is radially interior of the middle segments 137, and the low electric field area 150 is defined radially exterior of the high electric field area 148. The low electric field area 150 is the portion of the hollow core 118 extending radially between the middle segments 137 and the interfaces 153. The port hole 122 is formed to penetrate one of the interfaces 153 between two rings 134, which is in the low electric field area 150. Thus, although the port hole 122 penetrates the inner porous microstructure 132, the port hole 122 does not disrupt the inner porous microstructure 132 along the high electric field area 148, where most of the light energy propagates through. Thus, the port hole 122 shown in FIG. 3 causes little to no scattering and/or attenuation of the light energy propagating through the hollow core 118.

Figure 4:
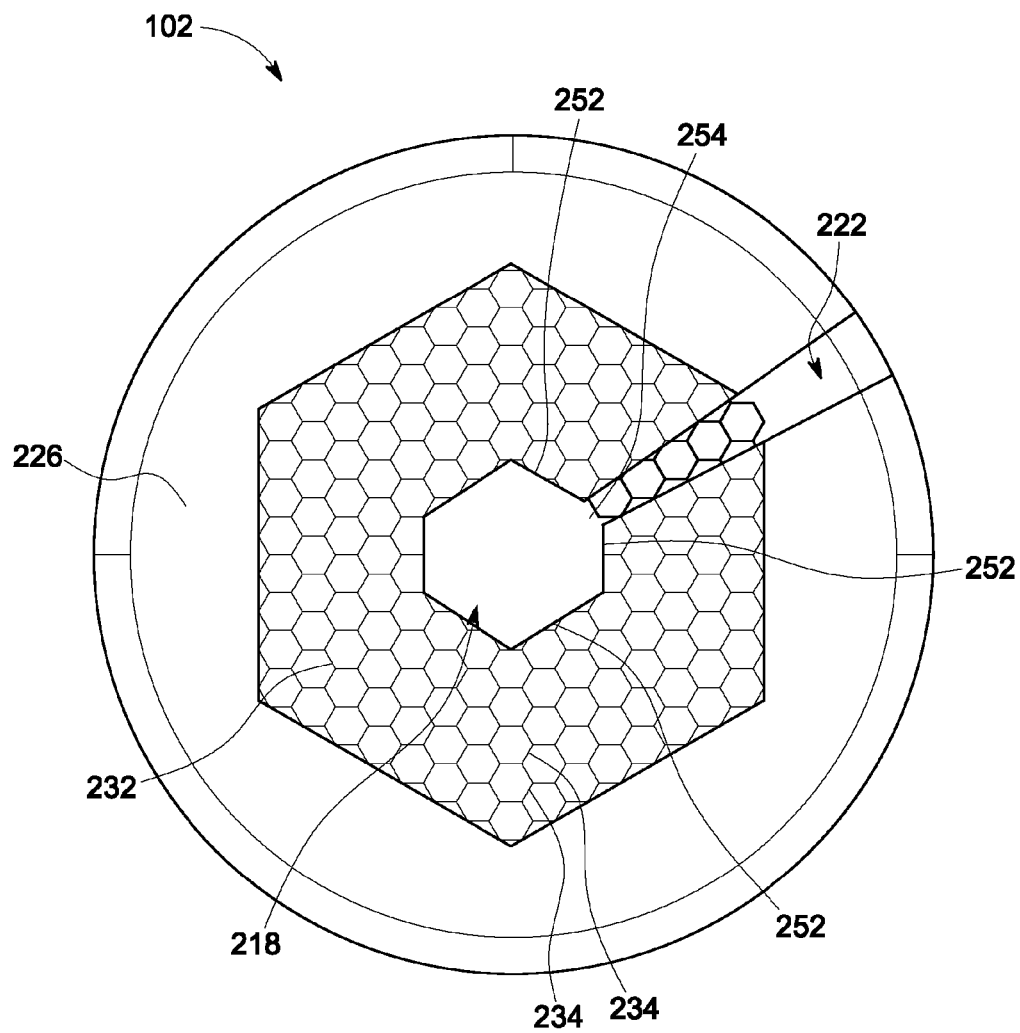
FIG. 4 is a cross-sectional view of the MOF of the gas sensing system of FIG. 1 according to an alternative embodiment.

FIG. 4 is a cross-sectional view of the MOF 102 of the gas sensing system 100 of FIG. 1 according to an alternative embodiment. The MOF 102 shown in FIG. 4 includes an outer cladding 226 surrounding an inner porous microstructure 232 that defines a hollow core 218. The inner porous microstructure 232 is comprised of a plurality of hollow tubes 234. The inner porous microstructure 232 and the core 218 are both hexagonally shaped. The perimeter contour of the core 218 includes six sides 252. The MOF 102 shown in FIG. 4 is a photonic crystal fiber that uses photonic bandgap principles to confine the light to the core 218. The MOF 102 includes a port hole 222 that extends radially into the core 218 and penetrates the perimeter contour of the hollow core 218 at a vertex 254 between two adjacent sides 252. The MOF 102 shown in FIG. 4 was modeled using electromagnetic theory, and the field amplitude along the fiber for the primary mode of photonic bandgap fiber with the port hole 222 entering the core 218 at a 30° angle had a mode index of $0.99822+i(1.02709\times10^{-5})$.

Figure 5:
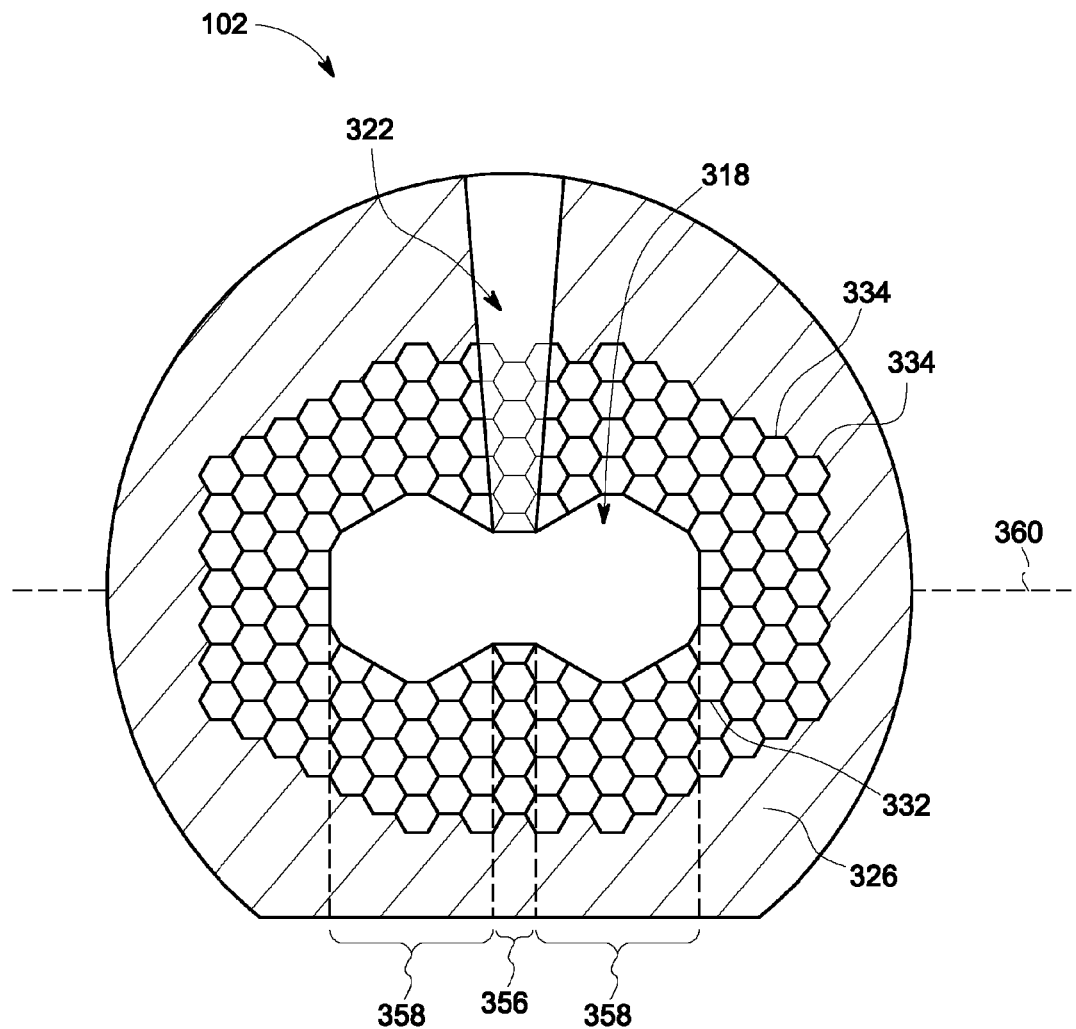
FIG. 5 is a cross-sectional view of the MOF of the gas sensing system shown in FIG. 1 according to another alternative embodiment.

FIG. 5 is a cross-sectional view of the MOF 102 of the gas sensing system 100 shown in FIG. 1 according to another alternative embodiment. The MOF 102 of FIG. 5 is a photonic bandgap structure fiber similar to the MOF 102 shown in FIG. 4, but an inner porous microstructure cladding 332 of the MOF 102 has been modified to primarily support an antisymmetric mode of the light energy propagating through the fiber 102.

Optical fiber is generally designed as either "single mode" or "multimode" fiber. In the former case, the fiber cross section is designed so that light of only one (or at most two orthogonal polarizations) electric field profile or "mode" with a specific effective refractive index or "mode index" can propagate along the fiber. This single propagating mode generally has its highest electric field amplitude in the center of the core, with the field amplitude decaying generally similarly to a Gaussian profile away from the center of the core. Multimode fibers, on the other hand, generally have a much larger core diameter and are able to support multiple propagating modes, each with a different mode index. The "lowest order" mode in multimode fiber typically again has a Gaussian-like field profile with the peak electric field at the center of the core. The higher order modes in multi-mode fiber can have multiple high intensity regions within the core of the fiber. Single mode fiber may be preferable for sensing applications because higher order modes have stronger electric fields near the cladding of the fiber, are more easily scattered by defects in the fiber, and generally exhibit a larger attenuation with distance along the fiber. Moreover, the light propagates at different speeds for each mode within the multimode fiber, which can interfere with timing applications when it is necessary to determine how fast a pulse of light has transited the fiber.

One or more fibers described in this application are specifically designed so that the lowest order mode does not have a Gaussian-like electric field profile, but rather is a mode in which the electric field is zero near the center of the core. The electric field of the mode has different signs on either side of the center of the core. This electric field profile is called an "antisymmetric" mode profile. In one or more embodiments, the fiber design supports only a few higher order modes, such as only this one antisymmetric mode described with reference to FIG. 5.

One common occurrence in optical fibers is that the polarization of light tends to rotate as the beam propagates down the fiber. A secondary issue then is maintaining the waveguide mode in the correct polarization orientation to minimize interaction with the port hole. One technique for maintaining polarization orientation include adding solid sections of glass on either side of the core to introduce asymmetry, but the solid glass sections tend to absorb radiation, particularly in the mid-IR range, so such technique is not desirable. The MOF 102 shown in FIG. 5 is designed to maintain the polarization of the light through the fiber 102 to maintain a reduced interaction of the electric field of the light energy with the port holes 322 along the length of the fiber 102.

Like the other embodiments of the MOF 102 described herein, the inner porous microstructure cladding 332 (referred to as inner porous microstructure 332) of the MOF 102 is surrounded by an outer solid silica cladding 326 (referred to as outer cladding 326). The inner porous microstructure 332 surrounds and defines a hollow core 318. The inner porous microstructure 332 includes an array of hollow tubes 334 disposed side by side. The hollow tubes 334 optionally have a hexagonal cross-sectional shape. In the illustrated embodiment, a perimeter contour of the hollow core 318 has an oblong shape that includes a narrow section 356 between two wide sections 358. The terms "narrow" and "wide" are relative terms that represent widths of the oblong hollow core 318 extending from both sides of an elongate axis 360 of the core 318. Thus, the narrow section 356 of the core 318 has a reduced width as compared to the two wide sections 358 on either end of the narrow section 356. For example, the oblong core 318 may resemble an hourglass or bowtie shape. In an embodiment, the MOF 102 includes port holes that extend radially into the fiber 102 and penetrate the perimeter contour of the core 318 at the narrow section 356. One such port hole 322 is shown in FIG. 5.

Figure 6:
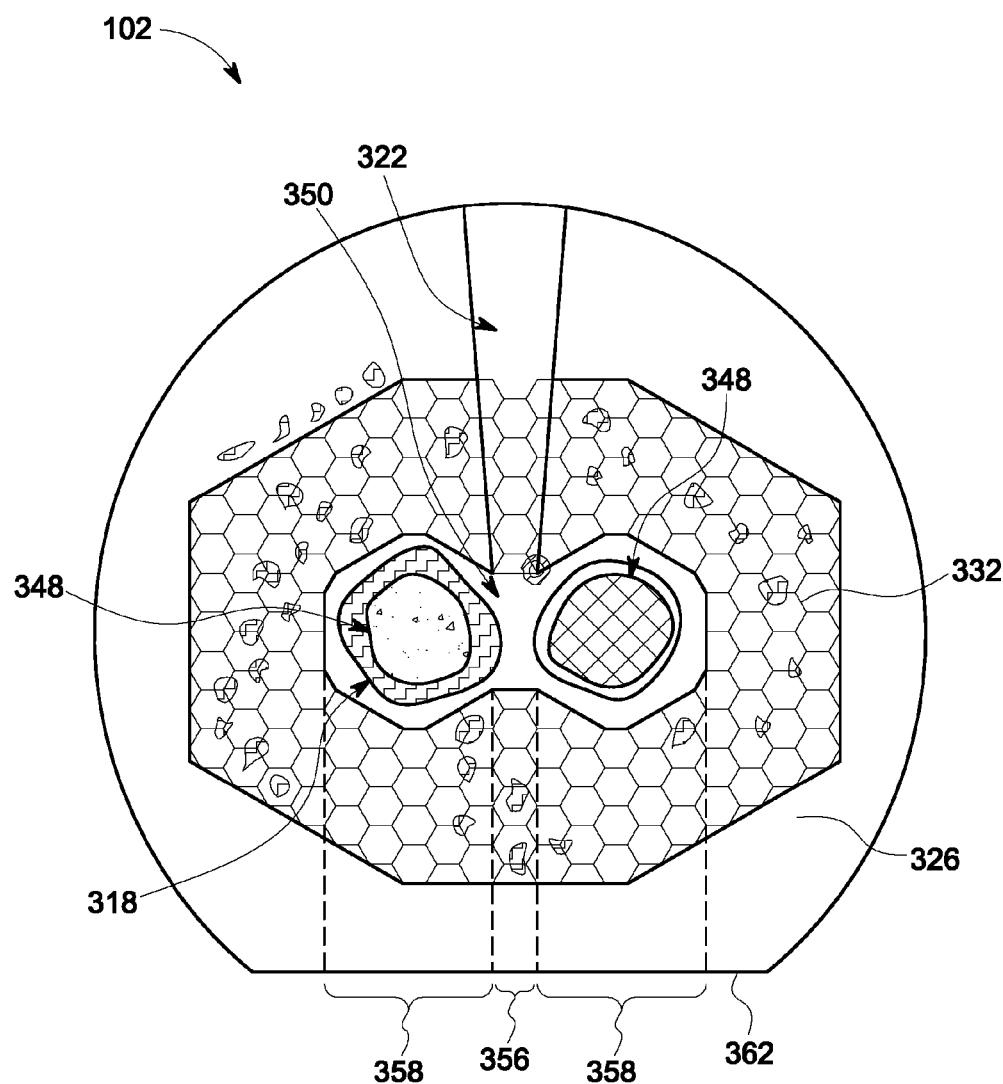
FIG. 6 is a cross-sectional view of the MOF of FIG. 5 depicting a modeled electric field profile for the primary mode of light energy within the hollow core.

FIG. 6 is a cross-sectional view of the MOF 102 of FIG. 6 depicting a modeled electric field profile for the primary mode of light energy within the hollow core 318. The oblong shape of the hollow core 318 supports an antisymmetric mode in the hollow core 318 in which the electric field has a null. This geometry can be used to enforce the "polarization maintaining" aspect for this fiber 102. For example, the perimeter contour of the hollow core 318 defines high electric field areas 348 within the two wide sections 358, and the perimeter contour defines a low electric field area 350 within the narrow section 356. A majority of the light energy in the hollow core 318 is disposed within the two wide sections 358 relative to the narrow section 356. For example, the electric field is positive along an axis in one of the wide sections 358, and the electric field in the other wide section 358 is negative along the same axis, such that the electric field defines a null or node between the two wide sections where the electric field is zero. The null is disposed within the narrow section 356. Thus, the electric field is small within the narrow section 356. The port hole 322 penetrates the perimeter contour of the core 318 at the narrow section 356 where the electric field is lowest. Thus, the location of the port hole 322 in the MOF 102 is configured to reduce light scattering and attenuation caused by the port hole 322 disrupting the inner porous microstructure 332. Upon modeling, the electric field amplitude for the primary mode along the fiber 102 with the port hole 322 penetrating the core 318 at the null as shown in FIG. 6 had a calculated mode index of $0.99817+i(3.28666\times10^{-5})$, which is close to the electric field amplitude along a similar fiber without any port holes, which had a mode index of $0.99826+i(3.10932\times10^{-5})$. Thus, port holes (e.g., port hole 322) formed in the MOF 102 have a low to negligible effect on light attenuation through the fiber 102.

The various embodiments of the MOF 102 shown in FIGS. 2-6 all have port holes that extend radially into the MOF 102 at specific orientations relative to the perimeter contours of the hollow cores to reduce light scattering and attenuation. But, since the hollow cores are not readily visible from outside of the fibers along the length of the fibers and the fibers are prone to twisting, the MOF 102 in various embodiments has one or more orientation features that provide information about the orientation of the hollow core to allow for accurate formation of the port holes in the specific locations described above.

In one embodiment shown in FIG. 6, the outer cladding 326 of the MOF 102 includes at least one planar segment 362 along a curved outer perimeter of the outer cladding 326. Only one planar segment 362 is shown in FIG. 6, but the outer cladding 326 may define more than one in other embodiments. The planar segment 362 may be formed during the formation of the MOF 102 or may be formed after forming the MOF 102, such as via polishing or otherwise removing a portion of the outer cladding 326. The planar segment 326 is specifically located relative to an orientation of the oblong perimeter contour of the hollow core 318. In the illustrated embodiment, the planar segment 326 is disposed parallel to the elongate axis 360 (shown in FIG. 5) of the core 318. In one embodiment, the port holes 322 may be formed by placing the planar segment 326 on a flat surface, and then forming the port holes 322 into an opposite side of the MOF 102 such that the port holes 322 are oriented perpendicular to the planar segment 326. In another embodiment, the port holes 322 may be formed through a center of the planar segment 326 in an orientation perpendicular to the planar segment 326. The port holes 322 may be formed by laser drilling methods or the like.

Figure 7:
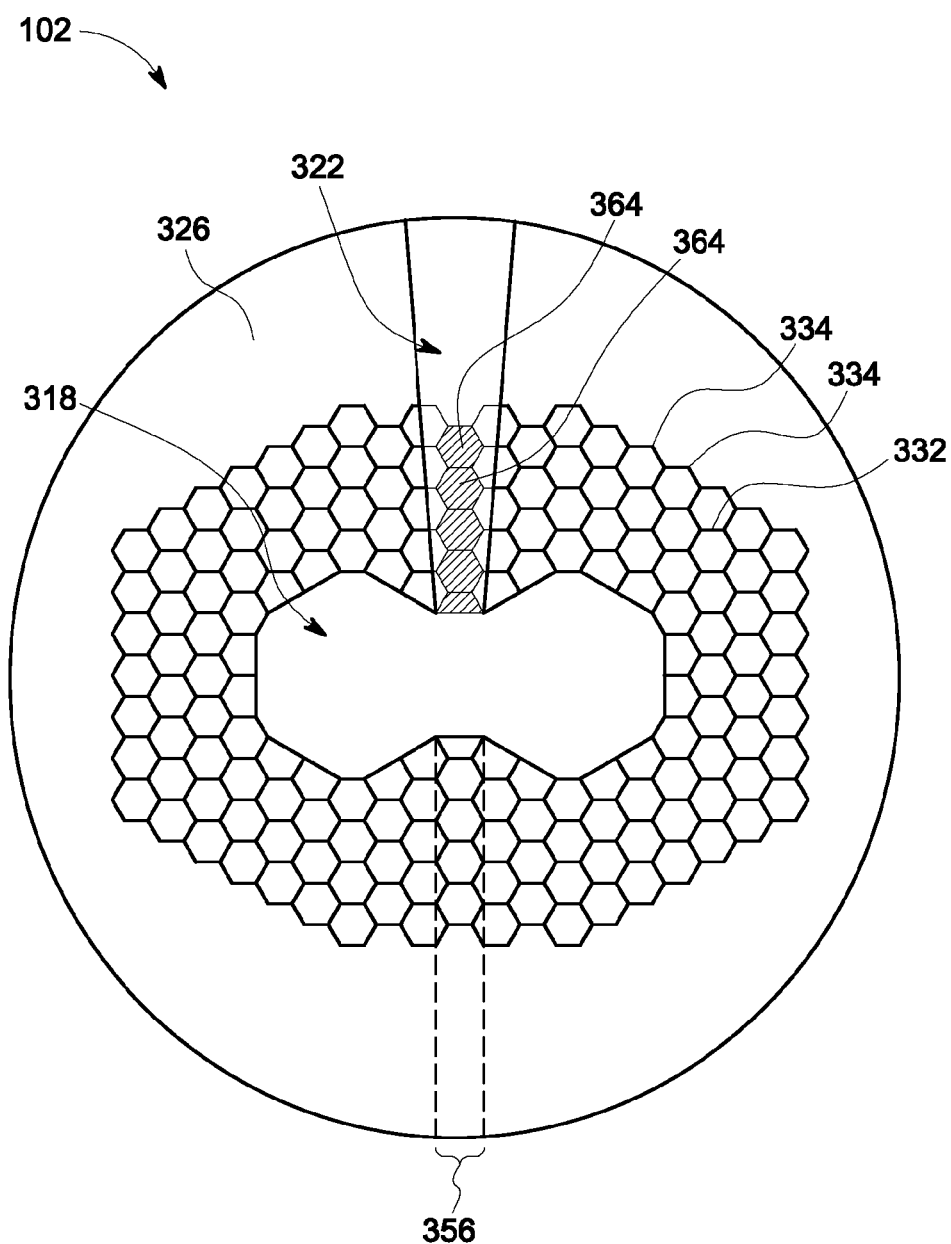
FIG. 7 is a cross-sectional view of the MOF according to the embodiment shown in FIGS. 5 and 6 in which the inner porous microstructure cladding includes several alignment rods disposed within the array of hollow tubes.

FIG. 7 is a cross-sectional view of the MOF 102 according to the embodiment shown in FIGS. 5 and 6 in which the inner porous microstructure 332 includes one or more alignment rods 364 disposed within the array of hollow tubes 334. The rods 364 are configured to provide guidance for forming the port holes 322 at the required specific locations and orientations relative to the hollow core 318. The rods 364 may be colored to allow for visual differentiation of the rods 364 relative to the hollow tubes 334. In the illustrated embodiment, the colored rods 364 align radially in a linear stack from the narrow section 356 of the perimeter contour of the core 318 outwards toward the outer cladding 326. For example, the inner porous microstructure 332 may be formed by assembling a pre-form of the hollow tubes 334, with the several colored rods 364 therein, and then drawing the pre-form to increase the length and reduce the diameter of the pre-form. The colored rods 364 may be hollow or solid, although the rods 364 are solid in the illustrated embodiment. The colored rods 364 are doped with a pigment or dye to have a color that is visible from outside of the MOF 102 looking through the outer cladding 326 via inspection by the naked eye or at least through a microscope. By visually identifying the colored rods 364, the MOF 102 may be properly oriented for the port hole formation process (e.g., laser drilling or the like). For example, the laser may drill through the linear stack of colored rods 364 to form the port holes 322. The colored rods 364 may be doped to be absorptive at the same wavelength or wavelength range as the laser used to drill the port holes 322, such that the rods 364 absorb the laser light and reduce the power needed for drilling.

Figure 8:
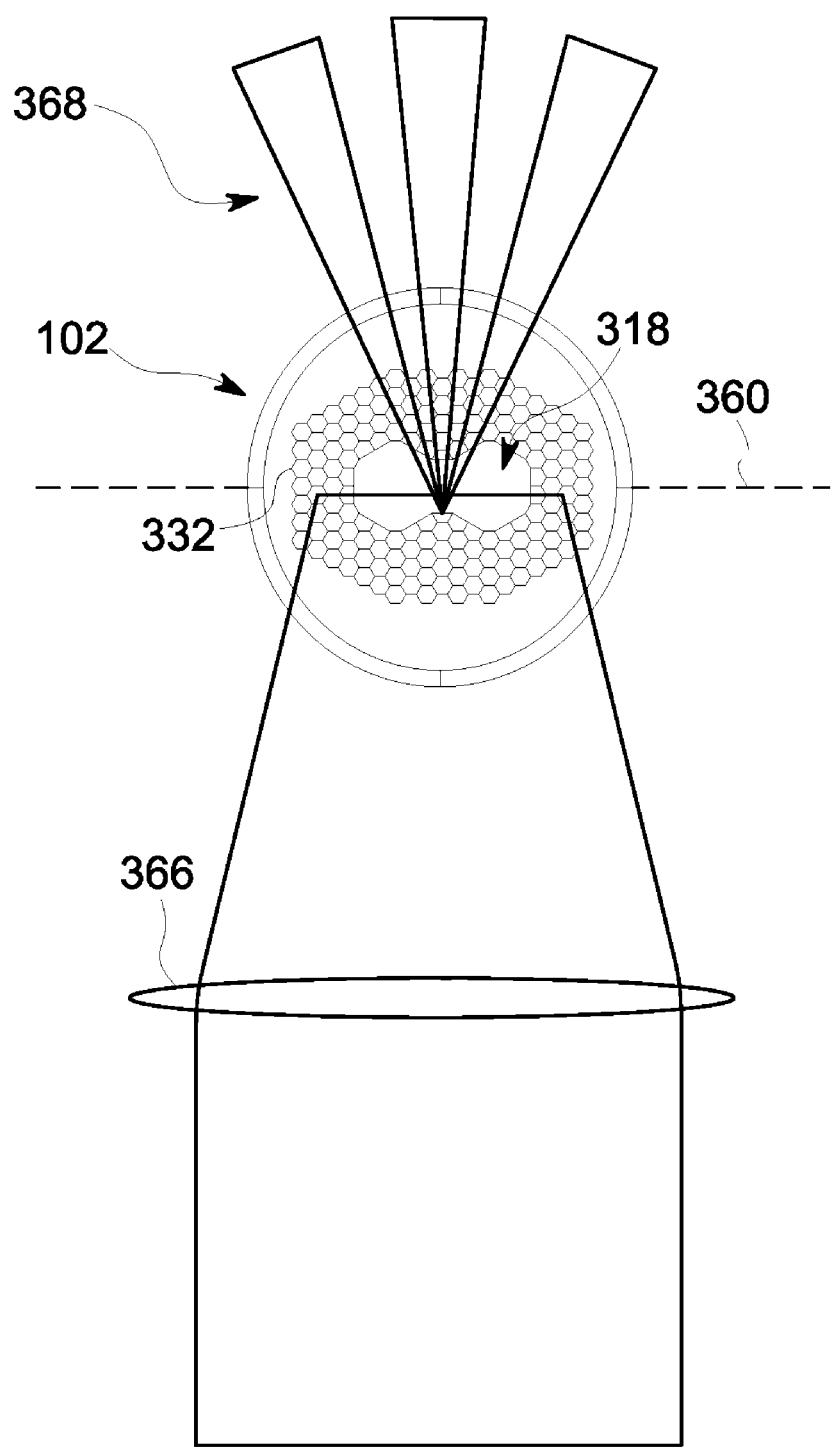
FIG. 8 is a schematic diagram showing a first diffraction pattern formed by illuminating the MOF according to the embodiment shown in FIGS. 5 and 6 from the side by a light source when the MOF is in a first rotational orientation.
Figure 9:
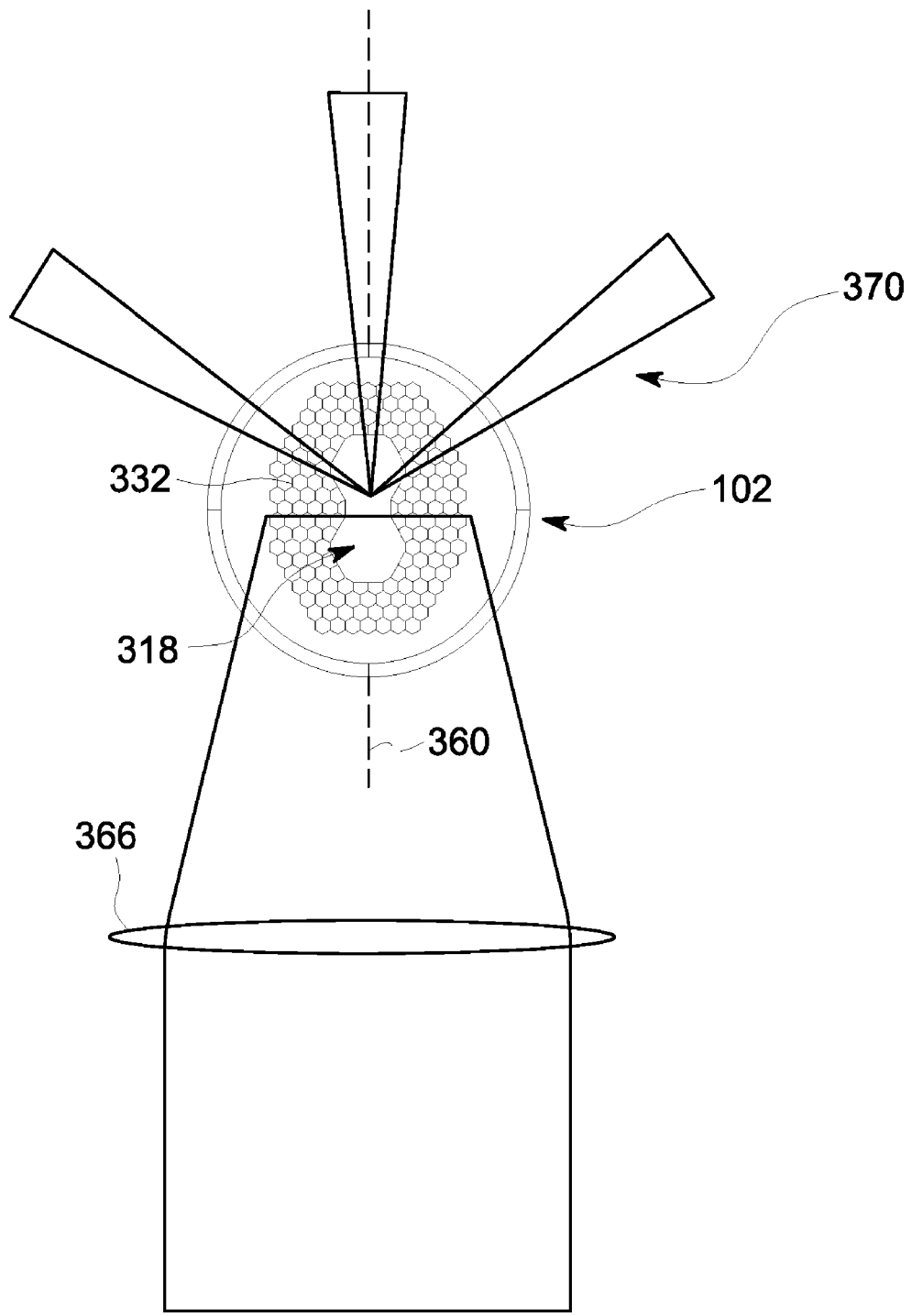
FIG. 9 is a schematic diagram showing a second diffraction pattern formed by illuminating the same MOF from the side by the light source when the MOF is in a first rotational orientation.

FIG. 8 is a schematic diagram showing a first diffraction pattern 368 formed by illuminating the MOF 102 according to the embodiment shown in FIGS. 6 and 7 from the side by a light source (not shown) when the MOF 102 is in a first rotational orientation. FIG. 9 is a schematic diagram showing a second diffraction pattern 370 formed by illuminating the same MOF 102 from the side by the light source when the MOF 102 is in a second rotational orientation. The light source may include a lens 366 that focuses light on the side of the MOF 102. The light source optionally may be a laser. Since the inner porous microstructure 332 of the MOF 102 exhibits a lattice pattern, the MOF 102 will diffract light that is focused onto the side of the MOF 102 in a complex diffraction pattern in the far field opposite to the light source. The symmetry of the inner porous microstructure 332 generates a symmetric diffraction pattern that changes based on the rotational orientation of the MOF 102 relative to the light source. The measurement of the diffraction pattern can be used to orient the MOF 102 for proper alignment and formation of the port holes 322 (shown in FIG. 5). The first light diffraction pattern 368 is narrower than the second light diffraction pattern 370. Thus, a perceived narrow diffraction pattern like the pattern 368 shown in FIG. 8 may be used to determine that the MOF 102 is oriented such that the elongate axis 360 of the oblong core 318 is perpendicular to the light path from the light source to the MOF 102. Furthermore, a perceived wide diffraction pattern like the pattern 370 shown in FIG. 9 may be used to determine that the MOF 102 is oriented such that the elongate axis of the oblong core 318 is parallel to the light path form the light source to the MOF 102.

Figure 10:
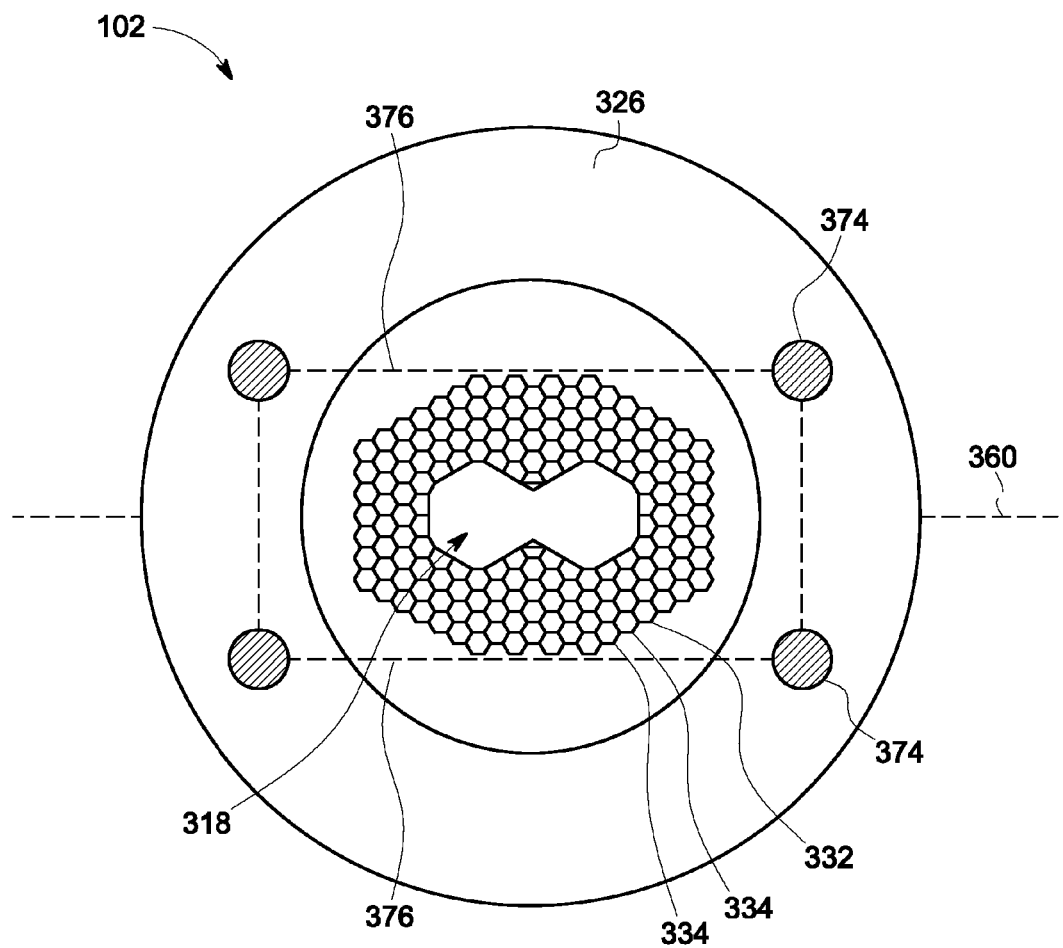
FIG. 10 is a cross-sectional view of the MOF according to the embodiment shown in FIGS. 5 and 6 in which the outer cladding includes multiple orientation rods disposed therein.

FIG. 10 is a cross-sectional view of the MOF 102 according to the embodiment shown in FIGS. 5 and 6 in which the outer cladding 326 includes multiple orientation rods 374 disposed therein that extend the length of the MOF 102. The orientation rods 374 are disposed outside of the inner porous microstructure 332. The orientation rods 374 are specifically located relative to an orientation of the oblong perimeter contour of the hollow core 318. For example, in the illustrated embodiment, four orientation rods 374 are arranged to define respective corners of a rectangle, in which the longer sides 376 of the rectangle are parallel to the elongate axis 360 of the core 318. Thus, the orientation of the rods 374 indicates the orientation of the perimeter contour of the core 318.

The orientation rods 374 are used to align the MOF 102 relative to the laser or other hole-formation tool for forming the port holes 322 (shown in FIG. 5). For example, the orientation rods 374 may form a diffraction pattern when the MOF 102 is illuminated from the side by a light source, as shown in FIGS. 8 and 9. The orientation rods 374 may be large compared to the tubes 334 in the inner porous microstructure 332 such that the rods 374 generate a diffraction pattern that may be more easily distinguishable from the diffraction pattern of the MOF 102 without such rods 374. The rods 374 may diffract light more efficiently than the MOF 102 itself due to the size, location, and/or absorptive characteristics of the rods 374. In the illustrated embodiment, the four rods 374 may generate a four-fold diffraction pattern to orient the MOF 102. Instead of being used to generate a diffraction pattern, the orientation rods 374 may be colored (e.g., doped with a pigment or dye) and configured to absorb ambient light such that the rods 374 are visible to the naked eye or via the use of a microscope. In another embodiment, the rods 374 may be formed of a material (such as silica doped with germanium) that fluoresces in the presence of light from certain wavelengths, such as natural light or ultraviolet light. The fluorescence is visible to the naked eye or via use of a microscope and can be used to orient the fiber 102. Since the rods 374 are arranged in a specific orientation relative to the core 318, the MOF 102 may be oriented for forming the port holes 322 based on the visual orientation of the rods 374. Although four rods 374 are shown, other numbers of rods may be used in other embodiments, as long as the rods have the same symmetry as the perimeter contour of the hollow core 318. Instead of, or in addition to the alignment rods 374, the MOF 102 may define holes that extend longitudinally through the outer cladding 326 and are used to diffract and/or absorb light for orienting the MOF 102.

Although the MOF 102 orientation techniques for port hole formation that are shown and described in FIGS. 7-10 refer to the embodiment of the MOF 102 shown in FIGS. 5 and 6, the same or at least similar techniques may be applied to the embodiments of the MOF 102 shown in FIGS. 2-4.

Figure 11:
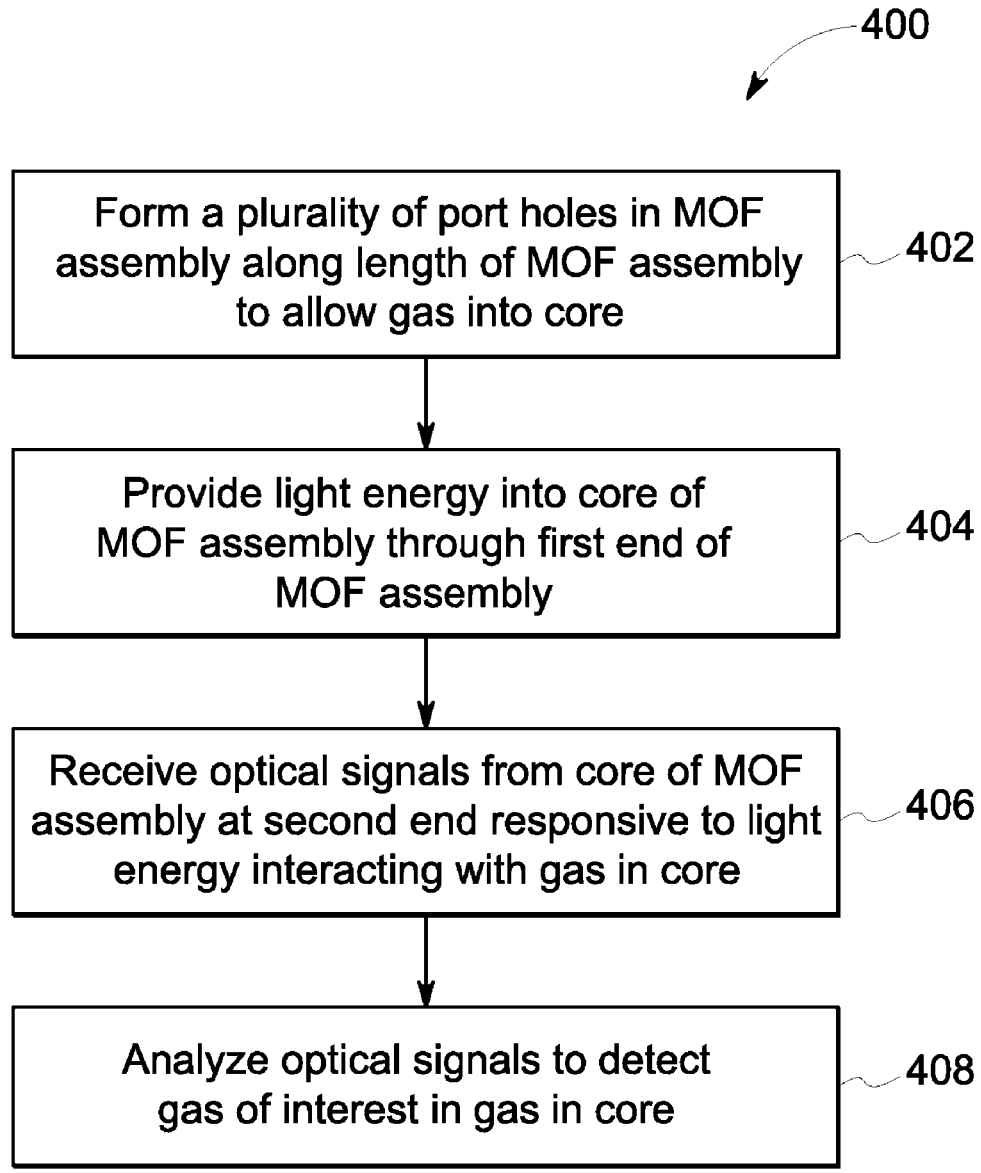
FIG. 11 is a flow chart of a method for detecting gas using a MOF according to an embodiment.

FIG. 11 is a flow chart of a method 400 for detecting gas using a MOF according to an embodiment. The method 400 may be performed using one or more of the embodiments of the MOF 102 shown and described herein, such as the embodiment of the MOF 102 shown in FIG. 2, the embodiment of the MOF 102 shown in FIG. 3, the embodiment of the MOF 102 shown in FIG. 4, and/or the embodiment of the MOF 102 shown in FIG. 5. At 402, multiple port holes are formed in the MOF along the length of the MOF to allow gas into a hollow core of the MOF. The port holes extend radially through an outer cladding and through an inner porous microstructure interior of the outer cladding to penetrate the hollow core. The port holes are oriented and located such that the port holes penetrate a portion of a perimeter contour of the hollow core that is a low electric field area, meaning that a low percentage (e.g., less than half) of an electric field of light that propagates through the hollow core passes through the area where the port holes are located.

At 404, light energy is provided into the hollow core of the MOF through a first end of the MOF. The light energy may be provided as a pulse of electromagnetic radiation, such as visible light or infrared light. In an embodiment, the light energy is in the mid infrared range. The light energy is provided by a light source. The light energy propagates through the hollow core and is reflected into the hollow core by the inner porous microstructure of the MOF.

At 406, optical signals form the hollow core of the MOF are received at a second end of the MOF. The optical signals are responsive to the light energy interacting with gas in the core. For example, the gas that is allowed into the core through the port holes may absorb and emit some of the light energy, which affects the optical signals received at the second end. The optical signals may be light energy that is different, at least slightly from the light energy provided to the hollow core at the first end due to the interaction with the gas in the hollow core. The optical signals may be received by a detection device.

At 408, the optical signals are analyzed to detect one or more gases of interest in the gas in the hollow core. For example, the optical signals may be analyzed using gas-phase infrared spectroscopy techniques. A gas of interest may be detected by comparing wavelengths of light that are determined to have been absorbed and emitted by the gas in the core to known wavelengths associated with specific gases. For example, a detected absorption band of 3.2 microns indicates that the gas in the core may include methane, which has a known absorption band at 3.2 microns. Detection of a gas of interest may include identifying the presence of the gas of interest and also may include determining a concentration of the gas of interest in the hollow core. Such information may be used to detect gas leaks in industrial settings, for example.

In an embodiment, a microstructured optical fiber (MOF) is provided that includes a cladding extending a length between a first end and an opposite second end. The cladding includes an inner porous microstructure that at least partially surrounds a hollow core through the cladding. The cladding defines a perimeter contour of the hollow core. The perimeter contour of the hollow core has a non-uniform radial distance from a center axis of the cladding such that first segments of the cladding along the perimeter contour have a shorter radial distance from the center axis relative to second segments of the cladding along the perimeter contour. The cladding is configured to receive and propagate light energy through the hollow core. The inner porous microstructure is configured to substantially confine the light energy within the hollow core. The cladding defines at least one port hole that extends radially from an exterior surface of the cladding to the hollow core. Each port hole penetrates the perimeter contour of the hollow core through one of the second segments of the cladding.

In an aspect, the second segments of the cladding include points along the perimeter contour that are at a maximum radial distance from the center axis.

In an aspect, walls of the inner porous microstructure that define at least portions of the perimeter contour have a negative curvature.

In an aspect, the at least one port hole is sized to allow gas into the hollow core from an external environment outside of the exterior surface of the cladding to interact with the light energy that propagates through the hollow core.

In an aspect, the first segments of the cladding are middle segments of walls of the inner porous microstructure, and the second segments of the cladding include end segments of the walls. The end segments have a greater radial distance from the center axis than the middle segments.

In an aspect, the second segments are located at interfaces between adjacent walls of the inner porous microstructure. Each second segment is defined by a respective end segment of the both adjacent walls.

In an aspect, the cladding further includes an outer solid layer circumferentially surrounding the inner porous microstructure. The outer solid layer defines the exterior surface of the cladding such that each port hole extends through the outer solid layer to the hollow core.

In an aspect, the inner porous microstructure defines gaps that extend from the center axis to an interior surface of the outer solid layer such that the perimeter contour of the hollow core is partially defined by the outer solid layer. The inner porous microstructure defines the first segments of the cladding along the perimeter contour. The second segments of the cladding along the perimeter contour are defined by segments of the interior surface of the outer solid layer that align with the gaps in the inner porous microstructure.

In an aspect, the outer solid layer includes at least one of orientation rods disposed therein or orientation holes defined therein that extend along the length of the cladding. The at least one of orientation rods or the orientation holes are specifically located relative to an orientation of the perimeter contour of the hollow core.

In an aspect, the cladding defines multiple port holes separated from each other in one or more longitudinal directions oriented along the length of the cladding.

In another embodiment, a microstructured optical fiber (MOF) is provided that includes a cladding extending a length between a first end and an opposite second end. The cladding defines an inner porous microstructure that at least partially surrounds a hollow core through the cladding. The cladding defines a perimeter contour of the hollow core. The perimeter contour of the hollow core has an oblong shape including a narrow section between two wide sections. The cladding is configured to receive and propagate light energy through the hollow core. The inner porous microstructure is configured to substantially confine the light energy within the hollow core. The cladding further defines at least one port hole that extends radially from an exterior surface of the cladding through the inner porous microstructure to the hollow core. Each port hole penetrates the perimeter contour of the hollow core at the narrow section. The at least one port hole is sized to allow gas into the hollow core from an external environment outside of the exterior surface of the cladding.

In an aspect, the inner porous microstructure includes an array of hollow tubes extending along the length of the cladding. The inner porous microstructure further includes multiple alignment rods disposed within the array of hollow tubes. The alignment rods are radially aligned in a linear stack from the narrow section of the perimeter contour of the hollow core outwards toward the exterior surface of the cladding. The port holes penetrate the alignment rods.

In an aspect, the cladding defines multiple port holes that are spaced apart from one other along the length of the cladding.

In an aspect, the two wide sections of the perimeter contour of the hollow core are high electric field areas and the narrow section of the perimeter contour is a low electric field area. A majority of the light energy propagating through the hollow core extends through the high electric field areas, and a minority of the light energy extends through the low electric field area.

In an aspect, the cladding further includes an outer solid layer circumferentially surrounding the inner porous microstructure. The outer solid layer defines the exterior surface of the cladding such that each port hole extends through the outer solid layer and the inner porous microstructure to the hollow core.

In an aspect, the outer solid layer includes at least one of orientation rods disposed therein or orientation holes defined therein that extend along the length of the cladding. The at least one of orientation rods or orientation holes are specifically located relative to an orientation of the oblong perimeter contour of the hollow core.

In an aspect, an outer perimeter of the outer solid layer is partially curved and includes at least one planar segment. The at least one planar segment is specifically located relative to an orientation of the oblong perimeter contour of the hollow core.

In another embodiment, a gas sensing system is provided that includes a microstructured optical fiber (MOF) and a light source. The MOF extends between a first end and an opposite second end. The MOF includes an outer solid cladding and an inner porous microstructure cladding circumferentially surrounded by the outer solid cladding. The inner porous microstructure cladding surrounds a hollow core. The inner porous microstructure cladding includes thin walls that define a perimeter contour of the hollow core. The MOF defines port holes spaced apart from each other along the length of the MOF. The port holes extend radially through the outer solid cladding and the inner porous microstructure cladding from an exterior surface of the outer solid cladding to the hollow core. The light source is optically coupled to the first end of the MOF and configured to provide light energy into the hollow core. The hollow core is configured to receive and propagate the light energy towards the second end of the MOF. The inner porous microstructure cladding is configured to substantially confine the light energy within the hollow core. The perimeter contour of the hollow core defines a high electric field area and a low electric field area such that a majority of the light energy propagating through the hollow core extends through the high electric field area and a minority of the light energy extends through the low electric field area. The port holes of the MOF penetrate the perimeter contour of the hollow core at the low electric field area. The port holes are configured to allow gas into the hollow core from an external environment outside of the exterior surface of the outer solid cladding to interact with the light energy within the hollow core.

In an aspect, the perimeter contour of the hollow core has a non-uniform radial distance from a center axis of the hollow core such that first segments of the inner porous microstructure cladding along the perimeter contour have a shorter radial distance from the center axis relative to second segments of the inner porous microstructure cladding along the perimeter contour. Each port hole penetrates the perimeter contour of the hollow core through one of the second segments of the cladding.

In an aspect, the perimeter contour of the hollow core has an oblong shape including a narrow section between two wide sections. Each port hole penetrates the perimeter contour of the hollow core at the narrow section.

In an aspect, the light source provides light energy to the hollow core that has a wavelength in the mid infrared range.

In an embodiment, a gas sensing system is provided that includes a microstructured optical fiber (MOF), a light source, a detection device, and one or more processors. The MOF extends between a first end and an opposite second end. The MOF comprises an outer cladding and an inner porous microstructure cladding disposed inside the outer cladding. The inner porous microstructure cladding surrounds a hollow core. The MOF defines port holes separated from each other in one or more longitudinal directions oriented along the length of the MOF. The port holes extend radially and continuously through the outer cladding and the inner porous microstructure cladding from the exterior surface of the outer cladding to the hollow core. The light source is optically coupled to the first end of the MOF and is configured to provide light energy into the hollow core. The hollow core is configured to receive and propagate the light energy along at least a portion of a length of the MOF. The inner porous microstructure cladding is configured to inwardly reflect the light energy toward the hollow core. A perimeter contour of the hollow core of the MOF defines a high electric field area and a low electric field area such that a majority of the light energy in the hollow core is disposed within the high electric field area relative to the low electric field area. Each port hole of the MOF penetrates the perimeter contour of the hollow core at the low electric field area. The port holes are configured to allow gas into the hollow core from an external environment outside of the outer cladding to interact with the light energy within the hollow core. The detection device is optically coupled to the second end of the MOF and configured to receive optical signals from the hollow core responsive to the light energy interacting with the gas in the hollow core. The one or more processors are operably connected to the detection device and configured to determine at least one of a presence or a concentration of one or more gases of interest in the core based on the optical signals received by the detection device.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A microstructured optical fiber (MOF) comprising:
a cladding extending a length between a first end and an opposite second end, the cladding defining an inner porous microstructure that at least partially surrounds a hollow core through the cladding, the cladding defining a perimeter contour of the hollow core, the perimeter contour of the hollow core having an oblong shape including a narrow section between two wide sections, the cladding configured to receive and propagate light energy through the hollow core, the inner porous microstructure configured to substantially confine the light energy within the hollow core, the cladding further defining at least one port hole that extends radially from an exterior surface of the cladding through the inner porous microstructure to the hollow core, each port hole penetrating the perimeter contour of the hollow core at the narrow section, the at least one port hole being sized to allow gas into the hollow core from an external environment outside of the exterior surface of the cladding.

2. The MOF of claim 1, wherein the inner porous microstructure includes an array of hollow tubes extending along the length of the cladding, the inner porous microstructure further including multiple alignment rods disposed within the array of hollow tubes, the alignment rods radially aligned in a linear stack from the narrow section of the perimeter contour of the hollow core outwards toward the exterior surface of the cladding, the port holes penetrating the alignment rods.

3. The MOF of claim 1, wherein the cladding defines multiple port holes that are spaced apart from one other along the length of the cladding.

4. The MOF of claim 1, wherein the two wide sections of the perimeter contour of the hollow core are high electric field areas and the narrow section of the perimeter contour is a low electric field area, a majority of the light energy propagating through the hollow core extending through the high electric field areas, and a minority of the light energy extending through the low electric field area.

5. The MOF of claim 1, wherein the cladding further includes an outer solid layer circumferentially surrounding the inner porous microstructure, the outer solid layer defining the exterior surface of the cladding such that each port hole extends through the outer solid layer and the inner porous microstructure to the hollow core.

6. The MOF of claim 5, wherein the outer solid layer includes at least one of orientation rods disposed therein or orientation holes defined therein that extend along the length of the cladding, the at least one of orientation rods or orientation holes being specifically located relative to an orientation of the oblong perimeter contour of the hollow core.

7. The MOF of claim 5, wherein an outer perimeter of the outer solid layer is partially curved and includes at least one planar segment, the at least one planar segment being specifically located relative to an orientation of the oblong perimeter contour of the hollow core.

* * * * *